(12) United States Patent
Clegg et al.

(10) Patent No.: US 7,913,841 B2
(45) Date of Patent: *Mar. 29, 2011

(54) TEMPORARY NEEDLE HOLDER WITH LATERAL NEEDLE HOLDER APERTURE

(75) Inventors: Trent Clegg, Lehi, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/290,935

(22) Filed: Nov. 30, 2005

(65) Prior Publication Data

US 2007/0119739 A1 May 31, 2007

(51) Int. Cl.
*B65D 85/24* (2006.01)

(52) U.S. Cl. .................... 206/366; 206/365; 206/370

(58) Field of Classification Search .......... 206/363–366, 206/369, 370, 380, 382
See application file for complete search history.

(56) References Cited

U.S. PATENT DOCUMENTS

| | | | |
|---|---|---|---|
| 964,406 | A | 7/1910 | DeWitt |
| 4,243,140 | A | 1/1981 | Thrun |
| 4,380,292 | A | 4/1983 | Cramer |
| 4,530,429 | A | 7/1985 | Erickson |
| 4,919,264 | A | 4/1990 | Shinall |
| 4,936,449 | A | 6/1990 | Conard et al. |
| 5,265,724 | A * | 11/1993 | Dondlinger .................. 206/366 |
| 5,311,985 | A | 5/1994 | Suida |
| 5,417,505 | A | 5/1995 | Voorhees |
| 5,462,163 | A | 10/1995 | Berry |
| 5,538,132 | A | 7/1996 | Propp et al. |
| 5,626,230 | A * | 5/1997 | Shanley et al. ................ 206/571 |
| 5,850,917 | A | 12/1998 | Denton et al. |
| 5,967,778 | A * | 10/1999 | Riitano ........................... 433/77 |
| 5,975,295 | A | 11/1999 | Diamond |
| 6,279,743 | B1 * | 8/2001 | Ballard et al. ................ 206/364 |
| 6,530,479 | B2 * | 3/2003 | Hernandez .................... 206/572 |
| 6,827,212 | B2 | 12/2004 | Reaux |
| 7,070,051 | B2 | 7/2006 | Kanner et al. |
| 7,159,714 | B2 | 1/2007 | Wilkinson et al. |
| 2003/0024891 | A1 | 2/2003 | Diamond |
| 2007/0119738 | A1 | 5/2007 | Clegg et al. |
| 2007/0119740 | A1 | 5/2007 | Clegg et al. |

OTHER PUBLICATIONS

Office Action dated Nov. 27, 2009 for U.S. Appl. No. 11/538,761.
Office Action dated Jan. 22, 2009 for U.S. Appl. No. 11/538,761.
Office Action dated Jan. 12, 2010 for U.S. Appl. No. 11/538,767.
Office Action dated May 29, 2009 for U.S. Appl. No. 11/538,767.
Office Action dated Sep. 5, 2008 for U.S. Appl. No. 11/538,767.

(Continued)

*Primary Examiner* — Mickey Yu
*Assistant Examiner* — Sharon M Prange
(74) *Attorney, Agent, or Firm* — Stoel Rives LLP

(57) ABSTRACT

A temporary needle holder having one or more lateral surface needle holder apertures configured to receive needles therein. The lateral surface needle holder aperture is provided in addition to a top surface needle holder field and is positioned in the side of the temporary needle holder allowing sharp implements to be inserted into the lateral surface needle holder aperture to minimize tipping of the temporary needle holder. A portion of the implement positioned in the lateral needle holder aperture can rest on the support surface on which the temporary needle holder is positioned. A boundary septum is provided between the lateral surface needle holder aperture and the needle holder field on the top surface to prevent passage of the needle apparatus from the need stop field to the lateral surface needle holder aperture to prevent an inadvertent stick or puncture the skin of a practitioner.

25 Claims, 6 Drawing Sheets

OTHER PUBLICATIONS

International search report and written opinion for PCT/US2006/061355 dated Nov. 29, 2006.

Office Action dated Jul. 20, 2010 for U.S. Appl. No. 11/538,767.

Notice of Allowance dated Jul. 13, 2010 for U.S. Appl. No. 11/538,761.

Office Action dated Feb. 1, 2011 for U.S. Appl. No. 11/538,767.

* cited by examiner

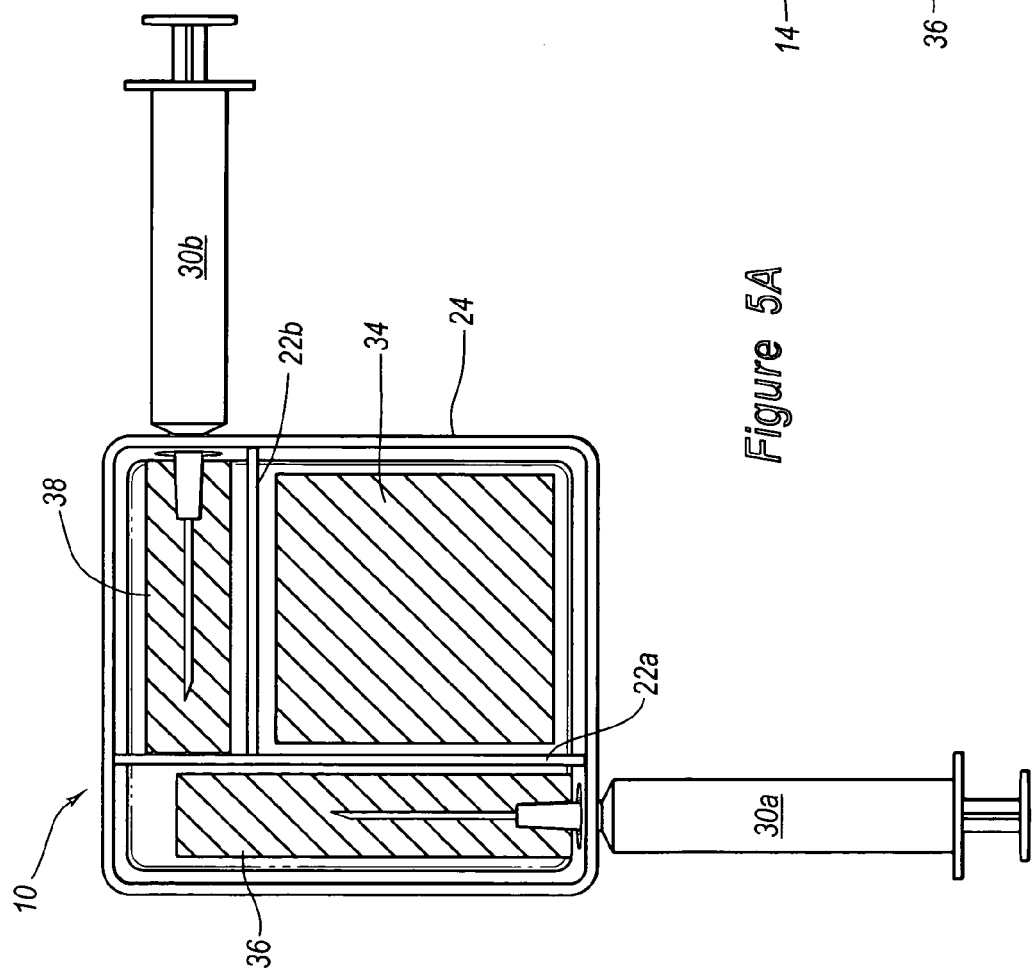
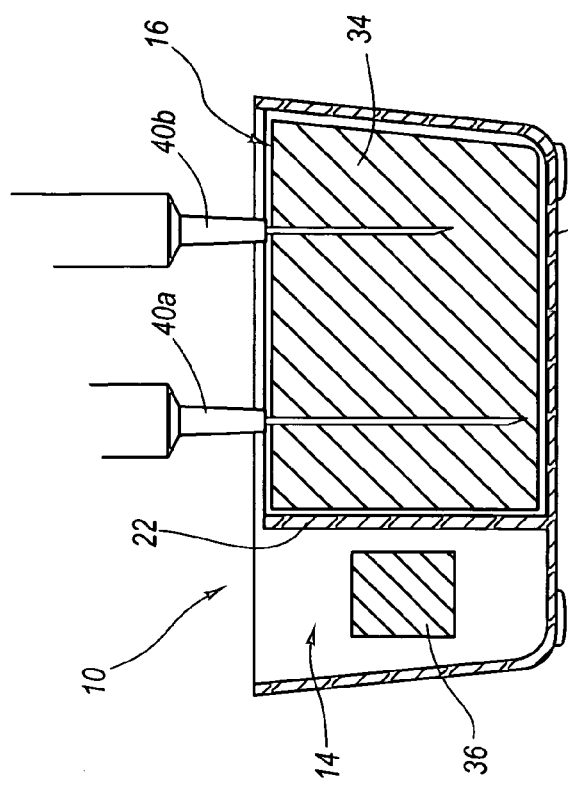
Figure 5A
Figure 5B

TEMPORARY NEEDLE HOLDER WITH LATERAL NEEDLE HOLDER APERTURE

BACKGROUND OF THE INVENTION

1. The Field of the Invention

The present invention relates to a temporary needle holder. In more particular, the present invention relates to a temporary needle holder having a lateral needle holder aperture.

2. Background and Relevant Art

In recent years, increased attention has been directed by medical practitioners and the medical community as a whole to blood borne illnesses and infections. The potential for the transmission of blood borne illnesses from patients to practitioners has heightened the awareness of safety standards to protect against inadvertent practitioner infection. A variety of new safety practices and regulations have been developed dictating procedures to be followed before, during, and after surgery as well as during the routine care of patients. For example, special procedures and cautions are recommended and/or required for interactions with patients involving bodily fluids, the handling of medical apparatus that have been utilized in connection with the bodily fluids of patients; and for the disposal of bodily fluids and other biological materials.

As a part of the new safety emphasis with regard to blood borne illnesses and infections, particular attention has been directed to the handling of needles, trocars, or other "sharps." Such sharps have been a subject of increased focus due to the potential for accidental puncture of the practitioner's skin and transmission of disease to the practitioner. A number of devices have been developed to protect against accidental punctures while utilizing sharps. For example, self-deploying needle shields, which can be readily actuated with limited risk of inadvertent puncturing of a practitioner, have been provided on a number of needles and other trocar type apparatus. Specialized depositories for the receipt and containment of used needles have also been developed which provide for safe and simple disposition of sharps.

Another type of device which has been developed to prevent needle sticks or other punctures of a practitioner are temporary needle holders. Such temporary needle holders are adapted to be utilized in a surgical field for holding a needle or other sharp implement that has been utilized or is intermittently utilized during the course of the procedure. Such temporary needle holders typically have a needle holder field in which the needles can be inserted while they are not being used. The temporary needle holder provides a location for the holding of needles that are not being utilized, such that the needles are not left on the surgical surface in a manner that they may inadvertently stick or puncture the skin of a practitioner during the course of the procedure.

Typically, such temporary needle holders are configured to be fairly small. Smaller temporary needle holders are typically desired due to surgical surface ergonomics and the fact that a limited number of needles are typically utilized in a procedure. For example, typically the number and types of surgical tools, implements, and containers placed in the surgical field for use during the procedure are sufficient that a limited amount of space is available for each apparatus. Due to the limited number of needles that are utilized in typical procedures, a fairly small temporary needle holder is sufficient to hold the number of needles needed during the procedure. Because a fairly small number of needles are typically utilized and the size requirements for additional needles are quite minimal, a larger unit is typically inefficient due to unused space on the needle holder field. Elimination of unused space on the needle holder field typically creates greater efficiencies in usage of materials, storage/shipping size, and per unit weight.

One problem associated with such smaller and/or lighter devices, is that where a practitioner is utilizing a larger needle and syringe combination or where the syringe is still partially filled with fluid, placement of the needle and syringe in the temporary needle holder can result in disadvantageous tipping of the temporary needle holder. Not only can such tipping be unpredictable, but the tipping can make it difficult to utilize the temporary needle holder and the needles and/or syringes positioned therein during the course of the procedure. Additionally, tipping of a partially filled syringe can result in turbulence in the contents of the syringe that may introduce air bubbles into the syringe. As a result, valuable surgical time may be consumed de-bubbling the syringe in preparation for injection of the contents of the syringe into the patient.

BRIEF SUMMARY OF THE INVENTION

The present invention is directed to a temporary needle holder having a lateral surface needle holder aperture configured to receive needles therein. Typically, the lateral surface needle holder aperture is positioned in a side surface of the temporary needle holder allowing needles, trocars, or other sharp implements to be inserted into the lateral surface needle holder aperture in a manner which minimizes tipping of the temporary needle holder.

In one embodiment, the lateral surface needle holder aperture is provided in addition to a top surface needle holder field. Thus, needle tips, or other needle apparatus, can be inserted into the needle holder field. Larger needles, or needles that are still partially filled with an injectate fluid, can be positioned in the lateral surface needle holder aperture. A portion of the syringe can rest on the support surface on which the temporary needle holder is positioned. Resting of the syringe on the support surface minimizes tipping of the temporary needle holder. When a syringe is positioned in the lateral surface needle holder aperture, the syringe is positioned out of the way of movement of the practitioner that may knock, result in breakage, or otherwise disrupt the syringe. Additionally, the unique position of lateral surface needle holder aperture allows a practitioner to easily and quickly identify and acquire a syringe positioned in the lateral surface needle holder aperture.

According to one embodiment of the present invention, a boundary septum is provided between the lateral surface needle holder aperture and the needle holder field on the top surface. The boundary septum provides a protective layer which prevents migration of the tip of a needle or other implement from the needle holder field to the lateral surface needle holder aperture. By preventing migration of the tip of the needle, potential breakage of a secondary needle apparatus by the migrating tip of a needle can be prevented. Preventing migration of the tip of the needle also minimizes the potential that the tip of the needle could inadvertently stick or puncture the skin of a practitioner. For example, the tip of the a needle can migrate from one needle holder field, pass through a secondary needle holder field, exit from a secondary needle holder aperture, and puncture the skin of the practitioner holding the temporary needle holder. In another embodiment, a plurality of lateral surface needle holder apertures are provided. The use of a plurality of lateral surface needle holder apertures allow the placement of two or more needles into lateral surface needle holder apertures.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5A is a cross-sectional view of a temporary needle holder, illustrating a plurality of needle tips inserted into a top needle holder cushion layer.

FIG. 5B is a top cross-sectional view illustrating a plurality of needle syringe combination units inserted into side needle holder cushion layers.

DETAILED DESCRIPTION OF THE PREFERRED EMBODIMENTS

The present invention is directed to a temporary needle holder having a lateral surface needle holder aperture configured to receive needles therein. Typically, the lateral surface needle holder aperture is positioned in a side surface of the temporary needle holder allowing needles, trocars, or other sharp implements to be inserted into the lateral surface needle holder aperture in a manner which minimizes tipping of the temporary needle holder.

In one embodiment, the lateral surface needle holder aperture is provided in addition to a needle holder field in a top surface of the needle holder aperture. Thus, needle tips, or other needle apparatus, can be inserted into the needle holder field. Larger needles, or needles that are still partially filled with an injectate fluid, can be positioned in the lateral surface needle holder aperture. A portion of the syringe can rest on the support surface on which the temporary needle holder is positioned. Resting of the syringe on the support surface minimizes tipping of the temporary needle holder. When a syringe is positioned in the lateral surface needle holder aperture, the syringe is positioned out of the way of movement of the practitioner that may knock, result in breakage, or otherwise disrupt the syringe. Additionally, the unique position of the lateral surface needle holder aperture allows a practitioner to easily and quickly identify and acquire a syringe positioned in the lateral surface needle holder aperture.

Figure 1:
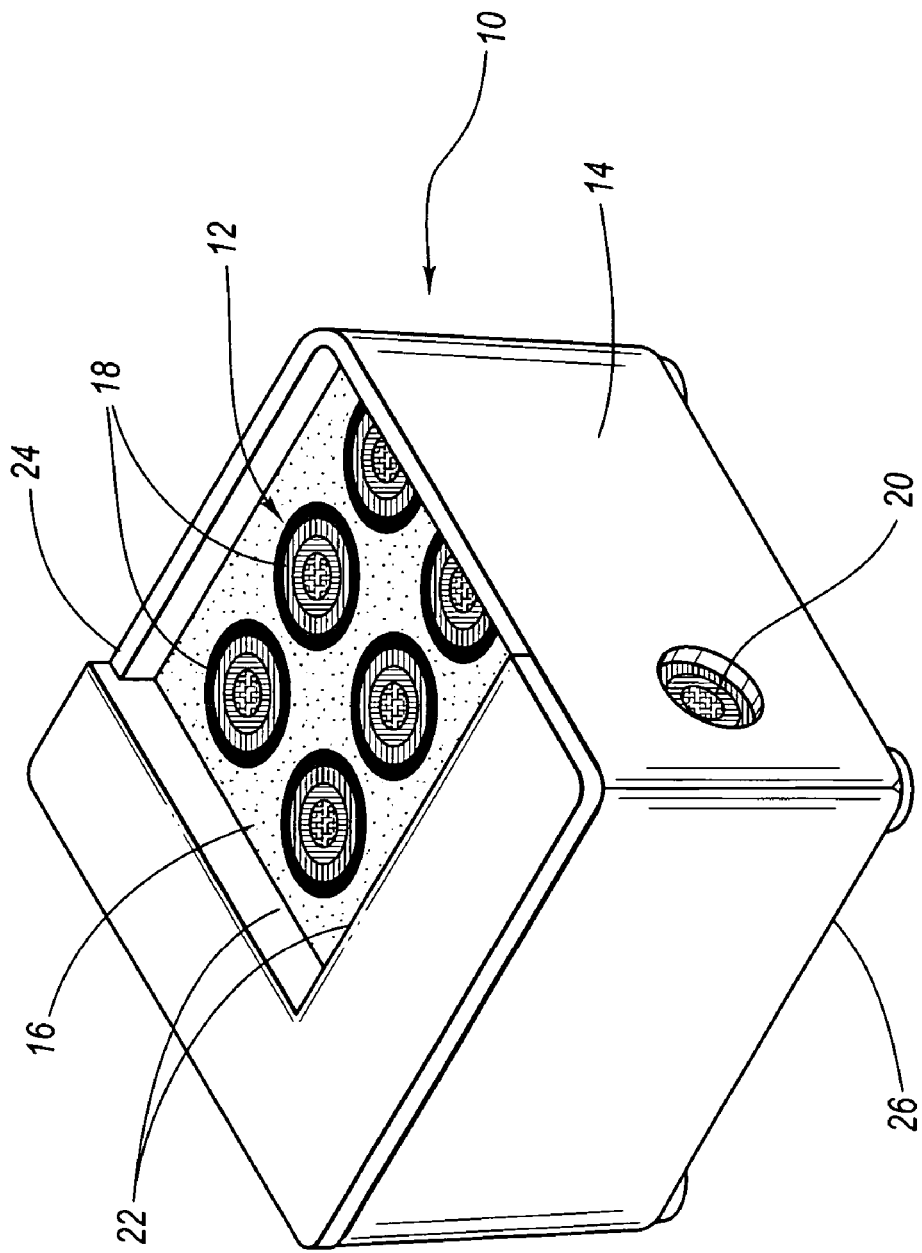
FIG. 1 is a perspective view of a temporary needle holder illustrating a lateral surface needle holder aperture.

FIG. 1 is a perspective view of temporary needle holder 10, according to one embodiment of the present invention. In the illustrated embodiment, temporary needle holder 10 has a lateral surface needle holder aperture 20, which is utilized to allow for insertion of needles into the side of the temporary needle holder 10 to minimize tipping of temporary needle holder 10. In the illustrated embodiment, temporary needle holder 10 includes a top surface 12, a side surface 14, a needle holder field 16, a lateral surface needle holder aperture 20, a boundary septum 22, a rim 24, and a bottom 26.

Top surface of temporary needle holder 12 includes needle holder field 16. Top surface 12 of temporary needle holder 10 is configured such that it is facing upward allowing it to be easily viewed and accessed by the practitioner. Targets 18 are positioned in the needle holder field to provide a visual identification of potential placement areas for needles, trocars, or other sharp implements or tools that have been utilized during the course of the procedure. A practitioner can insert smaller and/or lighter needle apparatus, such as needle tips, emptied syringes, or an IV trocar into top surface 12.

During the course of the procedure, it is not uncommon that a large needle, syringe, or other sharp implement may be utilized. Additionally, it is not uncommon that a syringe having a remaining amount of fluid positioned therein might need to be inserted into the temporary needle holder 10 during the course of the procedure. Lateral surface needle holder aperture 20 is positioned in the side surface 14 of the temporary needle holder 10 in a manner that the practitioner can insert larger and/or heavier needles and other sharp implements into the lateral surface needle surface aperture 20. Lateral surface needle holder aperture 20 provides not only a supplementary needle holder field for insertion of sharps devices, but is also positioned closer to the surgical surface, allowing for resting of the syringe, device, or implement on the surgical surface to minimize tipping of the temporary needle holder. The lateral surface needle holder aperture is one example of means for inserting a needle or other sharp device into a second side of the temporary needle holder.

Boundary septum 22 is positioned adjacent a lateral side of needle holder field 16. Boundary septum 22 comprises a hardened layer or other puncture impervious or puncture resistant layer configured to prevent the passage of the tips of needles, trocars, or other sharp implements from the needle holder field to the lateral surface needle holder aperture. Boundary septum 22 minimizes migration of needle tips into adjacent needle holder fields that may cause damage to the medical instruments. Boundary septum 22 also limits the passage of needle tips from needle holder field 16 to lateral surface needle holder aperture 20, or from lateral surface needle holder aperture 20 to needle holder field 16, in a manner that could catch the practitioner unaware and result in puncture of the practitioner's skin.

Rim 24 is positioned to provide an outer boundary for needle holder field 16. Rim 24 creates a slight recess between top surface 12 of a temporary needle holder 10 and the elevation of needle holder field 16. In this manner, rim 24 prevents inadvertent slipping of needles, sharps, or other implement from the top surface of the needle holder field 16 to the exterior of the temporary needle holder 10. In this manner, a practitioner can safely grasp the temporary needle holder 10 and insert a needle into the needle holder field 16. In the event that the needle slips or does not entirely puncture the needle holder field 16, the tip of the needle will typically be caught by rim 24, preventing additional slipping and puncturing of the practitioner in an unexpected manner.

Bottom 26 is positioned on the side of temporary needle holder opposite top surface 12. Bottom 26 is configured to be positioned on a surgical or other medical work surface on which the temporary needle holder is to be utilized. In one embodiment, bottom 26 includes a non-slip surface or adhesive surface which facilitates contact of the temporary needle holder 10 with the surgical surface and additionally prevents tipping of the temporary needle holder 10.

As will be appreciated by those skilled in the art, a variety of types and configurations of temporary needle holder can be provided without departing from the scope and spirit of the present invention. For example, in one embodiment, a different number and configuration of targets are provided in the needle holder field. In another embodiment, the lateral surface needle holder aperture is of a different size, shape and/or configuration. In another embodiment, the lateral surface needle holder aperture is provided in connection with the needle holder field on the top of the lateral surface needle holder aperture and is provided without a boundary septum.

Figure 2:
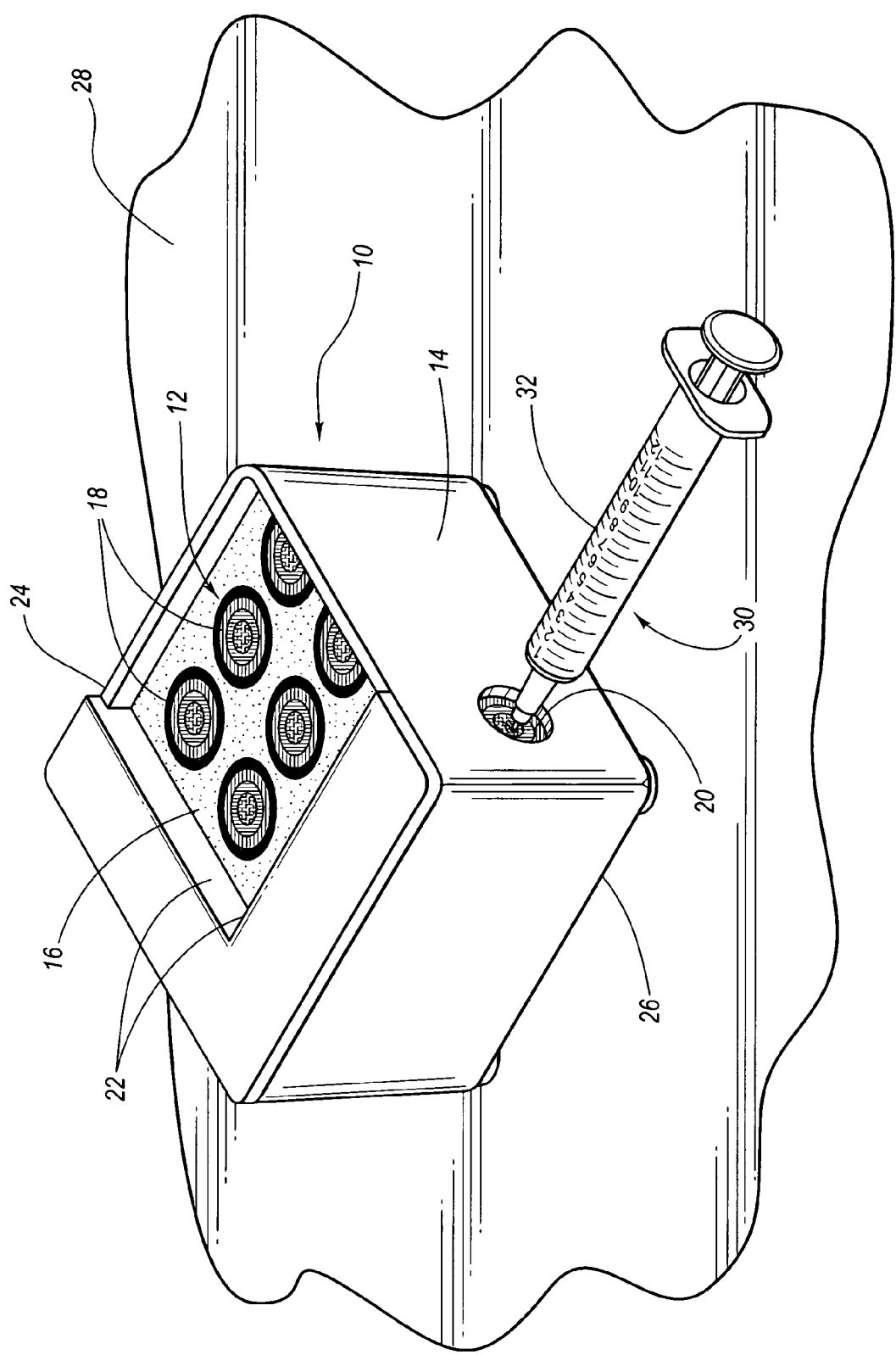
FIG. 2 is a perspective view of a temporary needle holder of FIG. 1, illustrating a needle inserted into the lateral surface needle holder aperture.

FIG. 2 is a perspective view of the temporary needle holder 10 of FIG. 1, illustrating a needle syringe combination 30 inserted into lateral surface needle holder aperture 20. In the illustrated embodiment, a syringe portion of needle syringe combination 30 is partially filled with a fluid 32. Fluid 32, positioned in the syringe portion of needle syringe combination 30, substantially adds to the weight of needle syringe combination 30. Additionally, the length of the needle portion of the needle syringe combination 30 creates a higher center of gravity, which can add to the likelihood of tipping of temporary needle holder 10 should needle syringe combination 30 be positioned or inserted in needle holder field 16. Additionally, a practitioner may simply desire to position needle syringe combination 30 in a separate location away from other needles or sharp implements. By providing a separate location for the insertion of needles and other sharps implements, needle holder field 16 can also help to more readily identify needle syringe combination 30 as an implement which the practitioner may desire to utilize later in the procedure being performed.

In the illustrated embodiment, needle syringe combination 30 is inserted in lateral surface needle holder aperture 20. Needle syringe combination 30 is shown positioned at a slight angle, such that the rearward portion of needle syringe combination 30 is in contact with support surface 28. By being in contact with support surface 28, needle syringe combination 30 is sufficiently supported to prevent breakage, or other damage, of needle syringe combination 30. Additionally, needle syringe combination 30 is supported in a manner that minimizes tipping of temporary needle holder 10. In this manner, desired and intended positioning of temporary needle holder 10 is maintained. This allows a practitioner to quickly identify needle holder field 16 for the insertion of additional needles, sharps, or other tools or implements, while also being able to quickly identify the positioning of lateral surface needle holder aperture 20 and needle syringe combination 30 positioned therein.

Figure 3:
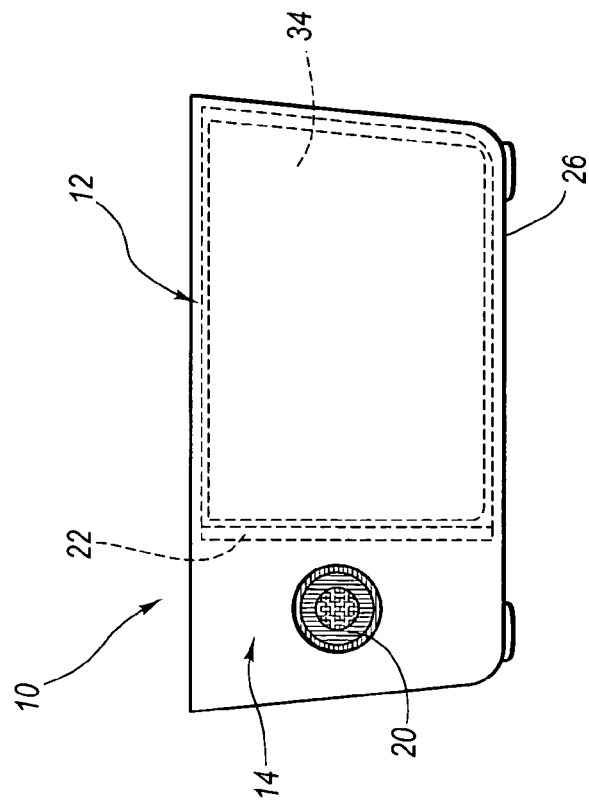
FIG. 3 is a side view of a temporary needle holder illustrating a top needle holder cushion layer, relative to a lateral surface needle holder aperture.

FIG. 3 is a side view of temporary needle holder 10, illustrating a top needle holder cushion layer 34 in phantom lines. The positioning of top needle holder cushion layer 34 relative to lateral surface needle holder aperture 20 is also shown. As previously discussed, lateral surface needle holder aperture 20 is positioned in side surface 14 of temporary needle holder 10. Top needle holder cushion layer 34 represents the total volume of the cushion layer associated with a needle holder field that is available to receive needles, trocars, or other sharp implements from the needle holder field.

In the illustrated embodiment, top needle holder cushion layer 34 extends a depth into temporary needle holder 10 which corresponds and even extends beyond the location of lateral surface needle aperture 20. Boundary septum 22 runs from top surface 12 of temporary needle holder 10 to the bottom 26 of temporary needle holder 10. In this manner, boundary septum 22 provides a complete and effective boundary to control the passage of needles, sharps, or other implements from needle holder cushion layer 34 to lateral surface needle holder aperture 20.

In the illustrated embodiment, the material from which top needle holder cushion layer 34 is formed, comprises a non-coring resilient foam material. The non-coring quality of cushion layer 34 allows a needle to be inserted into top needle holder cushion layer 34 and withdrawn without leaving a noticeable hole. In this manner, a secondary implement can be reinserted into the same position without weakening or minimizing the ability of cushion layer 34 to retain the secondary implement, subsequent to the earlier insertion.

As will be appreciated by those skilled in the art, a variety of types and configurations of temporary needle holder can be utilized without departing from the scope and spirit of the present invention. For example, in one embodiment the boundary septum extends only a portion of the length from the top surface of the needle holder cushion layer to the bottom of the needle holder cushion layer. In another embodiment a variety of types and configuration of cushion materials are be utilized. For example, in one embodiment, a thermal-plastic rubber layer can be utilized. In another embodiment, another resilient polymer-based material can be utilized. In another embodiment, small layers of foam can be positioned adjacent one another in a manner to retain a needle or other sharp implement.

Figure 4:
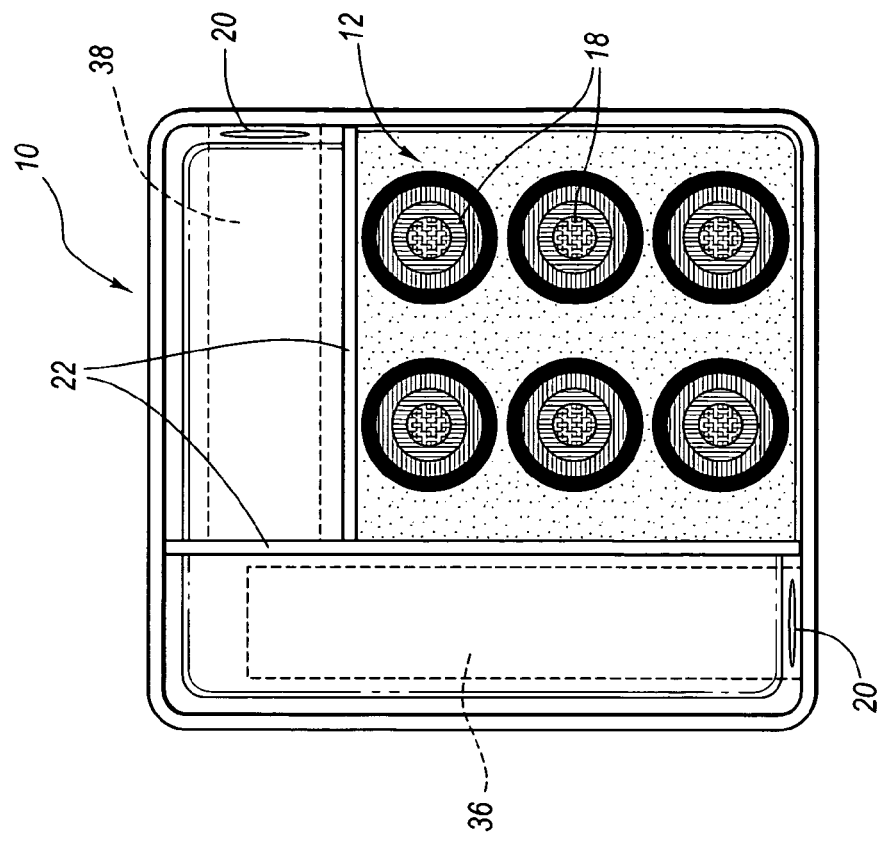
FIG. 4 is a top view of a temporary needle holder illustrating a plurality of side needle holder cushion layers associated with a plurality of lateral surface needle holder apertures.

FIG. 4 is a top view of the temporary needle holder illustrating the juxtaposition of the side needle holder cushion layers 36, 38 relative to the needle holder field. In the illustrated embodiment, side needle holder cushion layers 36, 38 are positioned on two sides of needle holder field 16. Side needle holder cushion layers 36, 38 extend along the length of the outer boundary of the needle holder field 16. As explained with reference to FIG. 3, boundary septum 22 provides an effective barrier between top needle holder cushion layer 34 and side needle holder cushion layers 36, 38. By providing first and second side needle holder cushion layers 36, 38, a practitioner can insert more than one implement into a lateral surface needle holder aperture. This allows the placement of multiple syringes in the event that multiple syringes may need to be utilized during the course of the procedure or in the event that multiple heavy needle/syringe combinations or other implements are utilized.

FIG. 5A is a top cross-sectional view of a temporary needle holder 10 according to one embodiment of the present invention. In the illustrated embodiment, the tips of needle syringe combinations 30*a* and 30*b* are inserted into side needle holder cushion layers 34 and 36. In the illustrated embodiment, it can be seen that the length of the needle syringe combinations 30*a* and 30*b* are sufficiently long that, in the absence of boundary septums 22*a*, 22*b*, the needles could extend from the side needle holder cushion layers 36, 38 and into the top needle holder cushion layer 34 and out of the associated needle holder field 16 (see also FIG. 5B). For example, where the practitioner carelessly inserts the needles of the needle syringe combinations 30*a*, 30*b* at an angle into the lateral surface needle holder apertures associated with side needle holder cushion layers 36, 38, the needles can extend from the side needle holder cushion layers 36, 38 and into the top needle holder cushion layer 34 and out of the associated needle holder field 16 (see FIG. 1).

Use of side needle holder cushion layers 36, 38 provides two additional points of placement for needles, trocars, or other sharp implements, in addition to the needle holder field 16 (see FIG. 1). Side needle holder cushion layers 36, 38 and their associated lateral needle holder apertures allow the practitioner to more easily keep track of particular needles, syringes, and associated medicinal fluids contained therein to be utilized in subsequent portions of the procedure. Additionally, the needles 30*a* and 30*b* can rest on the support surface on which the temporary needle holder 10 is positioned. This minimizes potential breaking of the tips of the needles 30*a*, 30*b* while also minimizing tipping of the temporary needle holder 10. In the illustrated embodiment, boundary septum 22*a* extends along the entire length of temporary needle holder 10, such that the tip of needle syringe combination 30*b* is prevented from contacting the tip of needle syringe combination 30*a* in a manner that may cause damage, the exchange of fluids, or other contamination of needle syringe combination 30*a* from needle syringe combination 30*b*.

FIG. 5B is a cross-sectional side view of a temporary needle holder 10 in which needle tips 40*a, b* have been inserted into a top needle holder cushion layer 34. In the illustrated embodiment, it can be seen that rim 24 of temporary needle holder 10 extends above the top surface of the needle holder field 16. Needle tips 40*a, b* have been inserted into top needle holder cushion layer 34, such that the distal ends of the needle tips 40*a, b* extend a given amount into the top needle holder cushion layer. The length of needle tip 40*a* is substantially longer than that of needle tip 40*b*. It can be appreciated that, in the absence of a boundary septum 22 and in the event that needle tip 40*a* is inserted at an angle into top needle holder cushion layer 34, the point of needle tip 40*a* could extend out through the side needle holder cushion layer 36 and associated lateral surface needle holder aperture 20 (see FIG. 1) in a manner that could result in inadvertent sticking or puncture of the practitioner who may be holding the temporary needle holder 10.

As will be appreciated by those skilled in the art, a variety of types and configurations of the temporary needle holder can be provided without departing from the scope and spirit of the present invention. For example, in one embodiment, the shape of the temporary needle holder is rectangular. In another embodiment, the shape of the temporary needle holder is other than a square or rectangle. In another embodiment, the sides of the needle holder cushion layers completely fill the inside of the temporary needle holder, such that the needle holder cushion layers are only bounded by the outside edges of the temporary needle holder and the boundary septa.

Figure 6A:
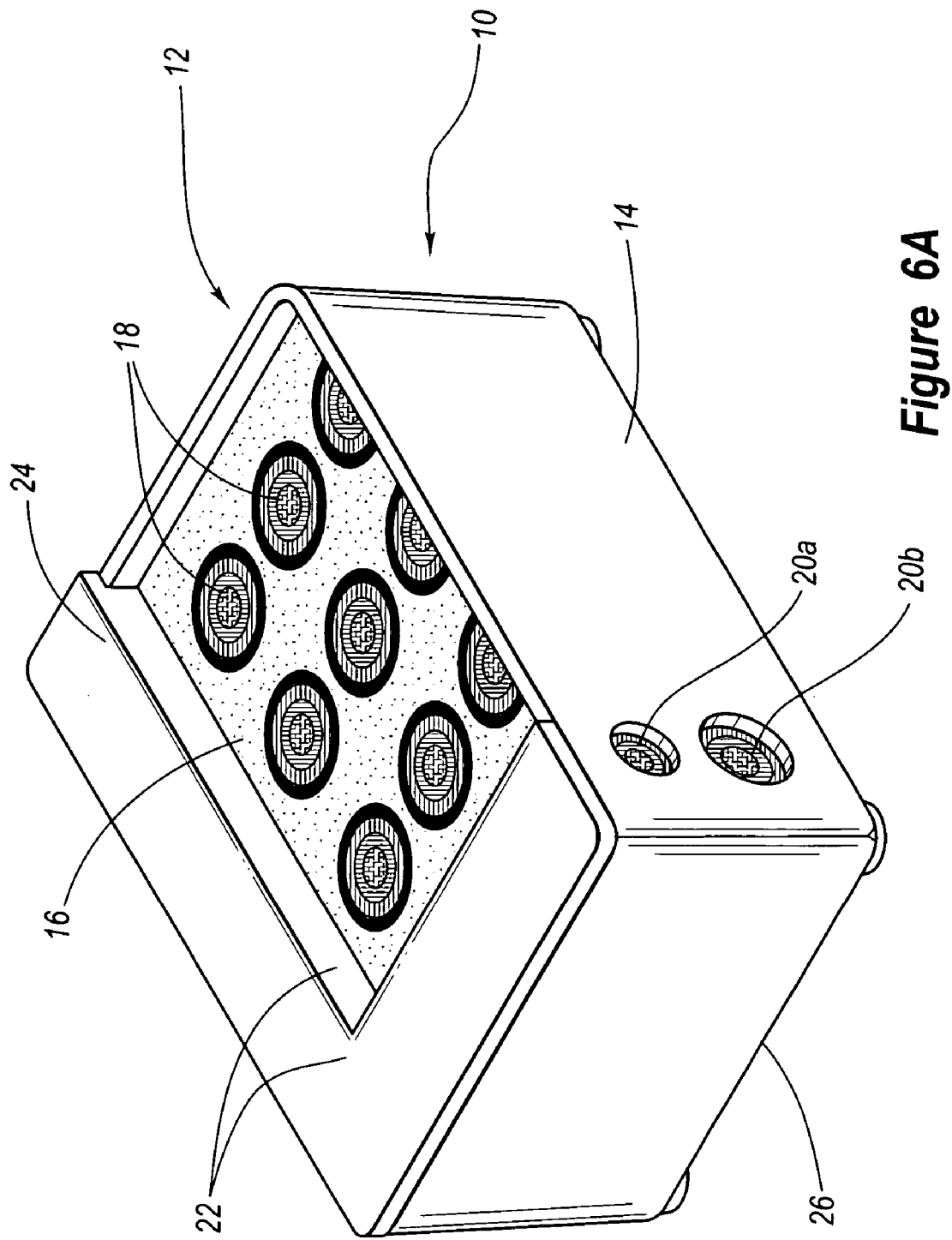
FIGS. 6A and 6B are perspective views of a temporary needle holder, according to alternative embodiments of the present invention.

FIG. 6A is a perspective view of an alternative embodiment of the present invention. In the illustrated embodiment, a first lateral surface needle holder aperture 20*a* and a second lateral surface needle holder aperture 20*b* are positioned in the side surface 14 of the temporary needle holder 10. In the illustrated embodiment, first lateral surface needle holder aperture 20*a* is positioned above second lateral surface needle holder aperture 20*b*. Second lateral surface needle holder aperture 20*b* is larger than first lateral surface needle holder aperture 20*a*. This allows larger needle syringe combinations to be placed in second lateral surface needle holder aperture 20*b*. As a result, a smaller needle syringe combination inserted into first lateral surface needle holder aperture 20*a* can rest directly on a larger needle syringe combination placed in second lateral surface needle holder aperture 20*b*. A plurality of lateral surface needle holder apertures can be provided in the same side surface of temporary needle holder 10, providing additional placement locations and potential sharps device organization by the practitioner during the course of the procedure.

Figure 6B:
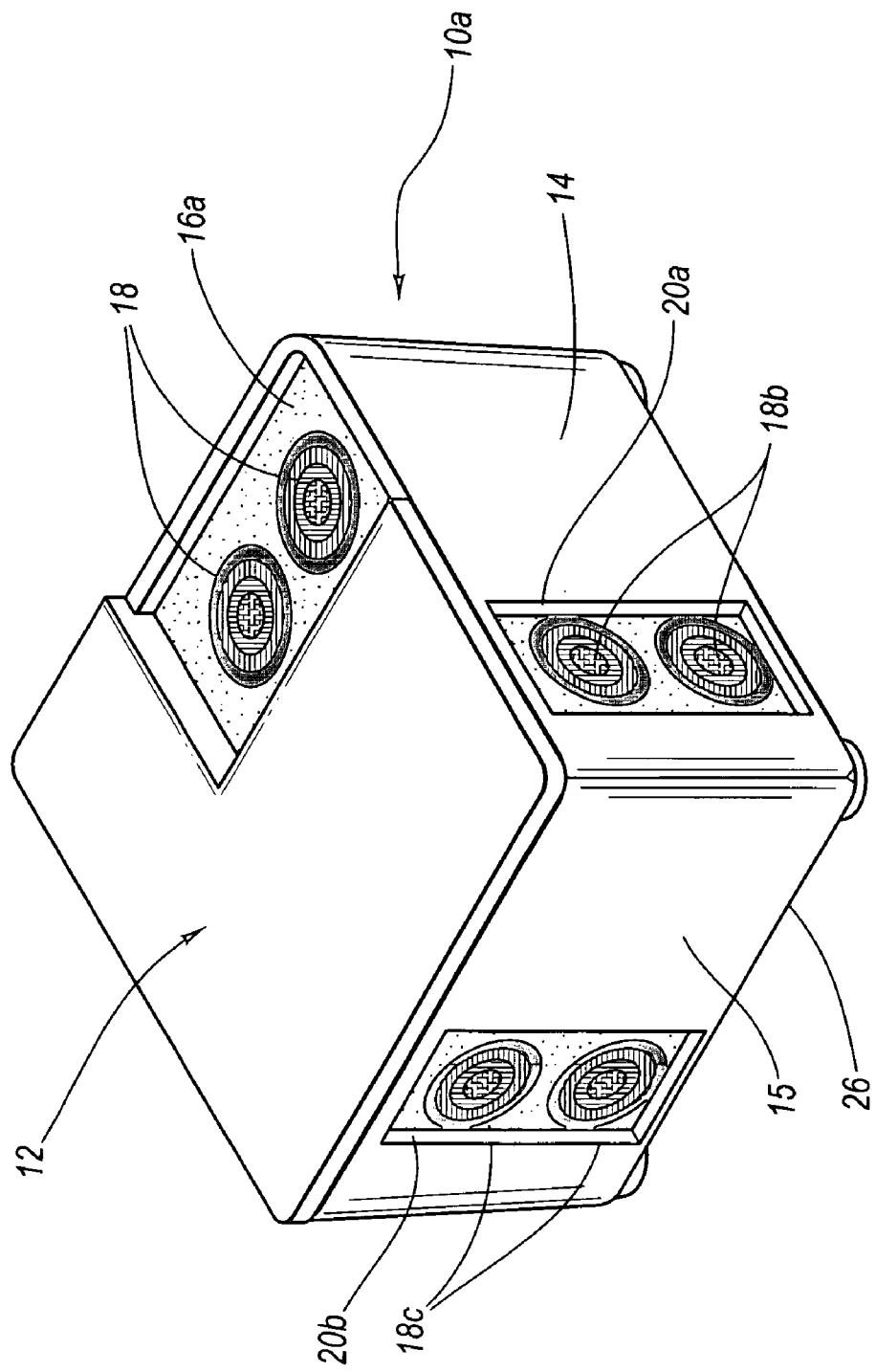

FIG. 6B is an illustrative view of a temporary needle holder 10*a*, according to one embodiment of the present invention. In the illustrated embodiment, a needle holder field 16*a* having two targets 18*a* is positioned in a top surface 12 of the temporary needle holder 10*a*. A lateral surface needle holder aperture 20*a* having two targets 18*b* is positioned in a second side surface 14 of temporary needle holder 10*a*. A second lateral surface needle holder aperture 20 having two targets 18*c* is positioned in a third second side surface 15. In this manner, both primary and secondary surfaces on the temporary needle holder are provided with substantially identical needle holder fields that can be utilized as desired by the practitioner. An arrangement as presently illustrated, in which the configuration of the needle holder fields are substantially the same, while being provided at different locations on the temporary needle holder, can be desirable where a procedure requires the organization and/or reuse of many similar sharp implements. Alternatively, a plurality of sharp implements which simply require repeated use and safe disposition throughout the course of the procedure may be utilized. According to one embodiment of the present invention, all or substantially all of the surfaces of the temporary needle holder are provided with a needle holder field, such that in the event that the temporary needle holder is tipped, a needle holder field is readily available for the disposition of needles, trocars, or other sharp implements that need to be disposed of.

According to one embodiment of the present invention, the temporary needle holder 10*a* is configured such that subsequent to the completion of the procedure, the entire temporary needle holder 10*a* can be discarded without needing to remove the needles that have been inserted therein. In this manner, the temporary needle holder 10*a* provides not only a safety mechanism for use during the course of the procedure, but also a quick, safe, and effective mechanism for disposing of the sharps subsequent to the completion of the procedure. Because lateral surface needle holder apertures 20*a* and 20*b* allow for the positioning of heavier needles, syringes, tools, or other implements, the temporary needle holder 10*a* functions not only as a sharps receptacle for smaller needle tips or lighter syringes, but also as a depository for all potentially sharp implements that may need to be discarded subsequent to the completion of the procedure.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A temporary needle holder configured to receive needles, trocars, or other devices or implements therein to minimize the exposure of such sharps to a surgical environment in a manner that could result in inadvertent puncturing of the skin of a practitioner subsequent to completion of the use of the device or implement, the temporary needle holder comprising:

a first needle holder cushion layer having a first needle holder field comprising an first insertion surface positioned in an upward facing surface of the temporary needle holder, the first needle holder cushion layer and the first needle holder field being configured to allow insertion of a needle or other sharp device therein and to retain the needle or other sharp device without assistance from the practitioner;

a side needle holder cushion layer having a side needle holder field comprising a second insertion surface positioned in a side surface of the temporary needle holder, the side needle holder cushion layer and the side needle holder field being configured to allow insertion of a needle or other sharp device therein and withdrawal of the needle or other sharp device there from, wherein the side needle holder cushion layer is configured to retain the needle or other sharp device without assistance from the practitioner;

a boundary septum positioned between the first needle holder field and the side needle holder field; and a top surface positioned adjacent the boundary septum, the top surface forming a covering to selectively enclose the side needle holder cushion layer, wherein the combination of the boundary septum and the top surface provide an effective boundary to prevent a needle or other sharp device which is positioned in the side needle holder cushion layer to extend from the side needle holder field to any secondary needle holder field in a manner that could result in the inadvertent puncture of the skin of the practitioner.

2. The temporary needle holder of claim 1, wherein when a needle or other sharp device is inserted into the insertion surface of the side needle holder field, a rearward portion of the needle or other sharp device can contact a support surface upon which the temporary needle holder is positioned and can be sufficiently supported by the support surface to prevent breakage or other damage to the needle or other sharp device and can minimize tipping of the temporary needle holder.

3. The temporary needle holder of claim 1, wherein the first needle holder cushion layer comprises a non-coring resilient foam material.

4. The temporary needle holder of claim 1, wherein the first needle holder cushion layer comprises a resilient polymer-based material.

5. The temporary needle holder of claim 1, further comprising one or more supplementary lateral needle holder fields.

6. A temporary needle holder configured to receive needles, trocars, or other devices or implements therein to minimize the exposure of such sharps to a surgical environment subsequent to completion of the use of the device or implement, the temporary needle holder comprising:

a first needle holder cushion layer having a first insertion surface in a first side of the temporary needle holder, the first insertion surface allowing insertion of a needle or other sharp device therein such that the first needle holder cushion layer retains the needle or other sharp device without assistance from the practitioner;

a side needle holder cushion layer having a needle holder aperture in a second side of the temporary needle holder such that the first insertion surface and the needle holder aperture are facing in different lateral directions, the needle holder aperture configured to allow the practitioner to insert a needle or other sharp device into a needle holder field of the side needle holder cushion layer to retain the needle or other sharp device without assistance from the practitioner;

a boundary septum between the first needle holder cushion layer and the side needle holder cushion layer, the boundary septum configured to prevent a needle or other sharp device inserted into the first needle holder cushion layer from exiting the temporary needle holder through the needle holder aperture, and wherein at least a portion of the first needle holder cushion layer is between the boundary septum and a side surface of the temporary needle holder; and a top surface positioned adjacent the boundary septum, the top surface forming a covering to selectively enclose the side needle holder cushion layer to prevent a needle or other sharp device which is positioned in the side needle holder cushion layer from extending to any secondary needle holder field in a manner that could result in the inadvertent puncture of the skin of the practitioner.

7. The temporary needle holder of claim 6, wherein the side needle holder cushion layer comprises a second insertion surface, and wherein the needle holder aperture is spaced from a bottom of the temporary needle holder such that when a needle or other sharp device is inserted in the second insertion surface of the side needle holder cushion, a rearward portion of a needle or other sharp device can contact a support surface upon which the temporary needle holder is positioned and can be sufficiently supported by the support surface to prevent breakage or other damage to the needle or other sharp device and can minimize tipping of the temporary needle holder.

8. The temporary needle holder of claim 6, wherein the first needle holder cushion layer comprises a non-coring resilient foam material.

9. The temporary needle holder of claim 6, wherein the first needle holder cushion layer comprises a resilient polymer-based material.

10. The temporary needle holder of claim 6, further comprising one or more supplementary lateral needle holder apertures.

11. The temporary needle holder of claim 10, wherein at least one of the one or more supplementary lateral needle holder apertures are positioned in the same side of the temporary needle holder as the needle holder aperture.

12. The temporary needle holder of claim 10, wherein at least one of the one or more supplementary lateral needle holder apertures are positioned in a different side of the temporary needle holder as the lateral needle holder aperture.

13. The temporary needle holder of claim 10, wherein each of the one or more supplementary lateral needle holder apertures comprise a needle holder cushion layer.

14. A temporary needle holder configured to receive needles, trocars, or other devices or implements therein to minimize the exposure of such sharps to a surgical environment subsequent to completion of the use of the device or implement, the temporary needle holder comprising:

a needle holder field having an insertion surface positioned in the upward facing surface of the temporary needle holder and having a first needle holder cushion layer, the needle holder field allowing insertion of a needle or other sharp device therein such that the needle holder cushion layer retains the needle or other sharp device, wherein at least a portion of the needle holder cushion layer is within the temporary needle holder;

a lateral needle holder aperture positioned adjacent a side needle holder cushion layer and being positioned in a side surface of the temporary needle holder such that the combination of the lateral needle holder aperture and the side needle holder cushion layer provides a single needle holder field, the lateral needle holder aperture allowing insertion of a needle or other sharp device into the side_ needle holder cushion layer to retain the needle or other sharp device; and a boundary septum positioned between the needle holder field and the lateral needle holder aperture to minimize the passage of the tip of a needle or other sharp implement from the needle holder field to the lateral needle holder aperture;

a top surface positioned adjacent the boundary septum, the top surface forming a covering to selectively enclose the side needle holder cushion layer, wherein the combination of the boundary septum and the top surface provides an effective boundary to prevent a needle or other sharp device positioned in the one needle holder cushion layer from extending to any secondary needle holder field in a manner that could result in the inadvertent puncture of the skin of the patient.

15. The temporary needle holder of claim 14, wherein the needle holder field comprises one or more targets positioned in the upper surface thereof.

16. The temporary needle holder of claim 14, wherein the lateral needle holder field includes one or a plurality of targets.

17. The temporary needle holder of claim 14, further comprising a rim positioned around an outside perimeter of the needle holder field.

18. A temporary needle holder configured to receive needles, trocars, or other devices or implements therein to minimize the exposure of such sharps to a surgical environment subsequent to completion of the use of the device or implement, the temporary needle holder comprising:

a needle holder cushion layer having a needle holder field at a first side of the temporary needle holder, the needle holder cushion layer allowing the practitioner to insert a needle or other sharp device therein such that the needle holder cushion layer retains the needle or other sharp device without assistance from the practitioner;

a lateral needle holding aperture for inserting a needle or other sharp device into a side needle holder cushion layer, wherein the lateral needle holding aperture is on a second side of the temporary needle holder such that the needle holder field of the needle holder cushion layer and the lateral needle holding aperture are facing in different lateral directions, and wherein the first side of the temporary needle holder is different from the second side of the temporary needle holder;

a boundary septum between the needle holder cushion layer and the lateral needle holding aperture, the boundary septum configured to prevent a needle or other sharp device inserted into the needle holder field in a top surface of the temporary needle holder from exiting the lateral needle holding aperture on the second side of the temporary needle holder, wherein at least a portion of the boundary septum is between at least a portion of the needle holder cushion layer that is within the temporary needle holder and at least a portion of the side needle holder cushion layer that is within the temporary needle holder; and a top surface positioned adjacent the boundary septum, the top surface forming a covering to selectively enclose the side needle holder cushion layer, the combination of the boundary septum and the top surface prevent a needle or other sharp device positioned in the lateral needle holding aperture from passing from the side needle holder cushion layer to the needle holder field at the first side of the temporary needle holder.

19. A temporary needle holder of claim 18, wherein the first side of the temporary needle holder comprises the top of the temporary needle holder.

20. A temporary needle holder of claim 18, wherein the first side of the temporary needle holder comprises a lateral side of the temporary needle holder.

21. A temporary needle holder of claim 18, wherein the first side of the temporary needle holder comprises the bottom of the temporary needle holder.

22. A temporary needle holder of claim 18, wherein the second side of the temporary needle holder comprises a lateral side of the temporary needle holder.

23. A temporary needle holder of claim 18, wherein the second side of the temporary needle holder comprises the bottom of the temporary needle holder.

24. A temporary needle holder of claim 18, wherein the first side of the temporary needle holder comprises a primary surface of the temporary needle holder.

25. A temporary needle holder of claim 24, wherein the second side of the temporary needle holder comprises a secondary surface of the temporary needle holder.

* * * * *